United States Patent [19]

Schwarz et al.

[11] Patent Number: 5,233,105
[45] Date of Patent: Aug. 3, 1993

[54] PROCESS FOR HALOGEN-FLUORINE EXCHANGE IN ORGANIC COMPOUNDS AND CATALYSTS FOR THIS PROCESS

[75] Inventors: Hans-Helmut Schwarz, Krefeld; Rudolf Braden, Odenthal, both of Fed. Rep. of Germany

[73] Assignee: Bayer Aktiengesellschaft, Leverkusen, Fed. Rep. of Germany

[21] Appl. No.: 603,582

[22] Filed: Oct. 25, 1990

[30] Foreign Application Priority Data

Oct. 28, 1989 [DE] Fed. Rep. of Germany ....... 3936024

[51] Int. Cl.⁵ ...................... C07C 17/20; C07C 17/08
[52] U.S. Cl. .................................. 570/160; 570/165; 570/166; 570/168; 570/169
[58] Field of Search ............... 570/168, 169, 166, 160, 570/165

[56] References Cited

U.S. PATENT DOCUMENTS

| 3,322,692 | 5/1967 | Clark | 570/169 |
| 3,591,646 | 7/1971 | Vecchio | 570/168 |
| 4,138,439 | 2/1979 | Schultz | 570/169 |

FOREIGN PATENT DOCUMENTS

| 1288085 | 1/1969 | Fed. Rep. of Germany | 570/166 |
| 1900241 | 7/1970 | Fed. Rep. of Germany | 570/166 |
| 1113658 | 5/1968 | United Kingdom | 570/166 |

*Primary Examiner*—Alan Siegel
*Attorney, Agent, or Firm*—Sprung, Horn, Kramer & Woods

[57] ABSTRACT

Bismuth/alkaline earth metal catalysts which contain 0.005–0.8 g-atom of bismuth per mol of the alkaline earth metal compound employed and can furthermore contain promoters and/or inert additives, and lanthanide catalysts with or without catalyst supports can be employed as catalysts for halogen-fluorine exchange in organic compounds by means of hydrogen fluoride.

7 Claims, No Drawings

PROCESS FOR HALOGEN-FLUORINE EXCHANGE IN ORGANIC COMPOUNDS AND CATALYSTS FOR THIS PROCESS

BACKGROUND OF THE INVENTION

1. Field of the Invention

The present invention relates to a process for exchanging halogen other than fluorine, preferably chlorine, for fluorine in organic compounds by means of hydrogen fluorine. The invention furthermore relates to bismuth/alkaline earth metal catalysts which contain 0.005–0.8 g-atom of bismuth per mol of the alkaline earth metal compound employed and can furthermore contain promoters and/or inert additives, and lanthanide catalysts with or without catalysts supports.

2. Description of the Related Art

A number of catalysts have been proposed for the exchange of halogen other than fluorine (mainly chlorine) for fluorine in halogenated organic compounds by means of hydrogen fluoride, the reaction chiefly being carried out in the gas phase, such as catalysts containing chromium and magnesium (European Patent 130,532), catalysts containing magnesium and iron and in addition copper and/or manganese (European Paten 235,547) and chromium oxide gels (U.S. Pat. No. 3,149,170); catalysts which consist of aluminum oxide containing halides of chromium, cobalt, nickel, copper, palladium or bismuth are furthermore known for the hydrofluorination of alkenes or fluoroalkenes to the associated fluorinated alkanes (DE-AS (German Published Specification) 1,900,241). Of the catalysts mentioned, the chromium oxide gels in particular have a high activity. However, their preparation and their use has the following disadvantages: When these gels are prepared from aqueous solution, considerable filtration difficulties must be reckoned with; however, the environmental measures which must be taken for disposing of chromium-containing residues form the preparation of these catalysts or of the spent chromium-containing catalysts themselves are of a particular and adverse significance.

There was therefore a need for processes for halogen-fluorine exchange in organic compounds using hydrogen fluoride, in particular in the gas phase, which can be carried out with a high fluorination activity and fluorination selectivity and which use catalysts which are free from chromium. The process according to the invention and the catalysts according to the invention meet this need.

SUMMARY OF THE INVENTION

A process has been found for exchanging halogen other than fluorine, in particular chlorine, for fluorine in organic compounds by means of hydrogen fluorine in the presence of a catalyst, which is characterized in that a chromium-free catalyst is used form the group comprising a) bismuth/alkaline earth metal catalysts which contain 0.005–0.8 g-atom of bismuth, preferably 0.008–0.7 g-atom of bismuth, per mol of the alkaline earth metal compound employed, and b) lanthanide catalysts of at least one lanthanide compound with or without catalyst supports.

The process according to the invention is accordingly above all characterized by the use of one of the catalysts mentioned under a) and b). It is of course also possible to employ several of the catalysts mentioned.

All the catalysts which can be employed according to the invention are distinguished by their lack of chromium.

The invention thus also relates to the bismuth catalysts mentioned above under a), which can furthermore contain promoters and/or inert additives.

In addition to bismuth, the catalysts according to the invention contain at least one compound of alkaline earth metals.

The invention furthermore relates to the lanthanide catalysts mentioned above under b).

DETAILED DESCRIPTION OF THE INVENTION

The alkaline earth metal compounds employed for the preparation of the catalysts mentioned under a) are preferably the carbonates, hydroxides, oxides and fluorides; at least one compound from the group comprising magnesium oxide, is particularly preferably employed. The alkaline earth metal compounds employed are charged or impregnated with one or more bismuth compounds, it also being possible for a double reaction to occur between the alkaline earth metal compound and the bismuth compound(s).

The catalysts according to the invention under a) can furthermore contain promoters which consist of compounds of elements of subgroups VII and VIII of the Periodic Table of the Elements (Mendeleev) and of the lanthanides. Examples of these are compounds of manganese, iron, cobalt, nickel, lanthanum, cerium and dysprosium. The catalysts can also carry more than one promoter. The gram atom ratio of the promoter elements to the element bismuth is 0.01–200:1, preferably 0.1–10:1.

The catalysts according to the invention can furthermore contain inert additives, for example graphite; however, they are preferably free from such inert additives.

To prepare the catalysts according to the invention, the alkaline earth metal compounds can be impregnated or sprayed with solutions of bismuth and the promoters in the customary manner. The alkaline earth metal compounds can furthermore be made into a paste with soluble or insoluble compounds of bismuth and of the promoters and water, after which shaped catalyst pieces are prepared from the doughy paste formed and are dried. In the case where soluble salts of bismuth and of the promoter elements and the alkaline earth metal compounds are made into a paste, a double reaction often occurs, for example between bismuth nitrate and calcium oxide. The preparation processes mentioned are known in principle to the expert.

In the present case, preparing a paste is the most elegant and advantageous preparation method and will therefore be described below in more detail. For this, the carbonates, hydroxides, oxides or fluorides of the alkaline earth metals are thoroughly mixed, for example, with water-soluble salts of bismuth and of the promoter elements in an aqueous medium at 5°–95° C. to establish reaction equilibrium. If inert additives are desired, these are likewise added in this phase. For better handling of the aqueous solution of bismuth salts and if appropriate promoter metal salts, a little acid is added in order to avoid hydrolysis and thus flocculation of basic salts. In principle, however, it is also possible to use sparingly soluble or insoluble basic salts of bismuth or of the promoter metals; nevertheless, in this procedure the reaction equilibrium is established more slowly.

To establish the reaction equilibrium, the preparation should be carried out for 1-5 hours with thorough mixing, since the mixing of the paste and a double reaction which takes place during this procedure takes place in a non-homogeneous phase system. The reaction equilibrium is furthermore established more quickly at elevated temperature up to 95° C.; in general, however, the process can be carried out at 20°-50° C., preferably at room temperature.

The amount of water used for mixing the paste is not critical for any double reaction which takes place, but is determined by simple preliminary experiments so that the pasty mass which forms can be processed by a kneader. The water, alkaline earth metal compounds and metal salts can in principle be added in an desired sequence.

The resulting paste is dried without being washed. It is suitable for preparation of shaped catalyst articles before or after drying. Since no washing out operation is included in this type of catalyst preparation, the atomic ratio of feed components is the same as that of the finished catalyst. In addition, no effluents which require disposal are formed. The shaped articles can be produced by the customary technical measures, such as, for example, pelletizing, extrusion or granulation.

After shaping, the shaped catalyst pieces are dried, which leads to shaped catalyst pieces of very high mechanical stability. Drying is carried out at 50°-150° C., preferably 70°-120° C.; this can be performed either under normal pressure or in vacuo. Drying is in principle also possible at room temperature, but then takes longer.

It has furthermore been found that the catalysts thus obtained undergo an increase in activity in the course of their use for fluorination of organic compounds by means of hydrogen fluoride. It is therefore preferable for the catalysts according to the invention to be activated by treatment with hydrogen fluoride before being used. This treatment with hydrogen fluoride is carried out at 20°-500° C., preferably 100°-500° C. and particularly preferably at 120°-420° C. This treatment leads to a substantial or complete replacement of the anions present by the fluoride anion. This treatment of the catalysts with hydrogen fluoride can advantageously be complemented by heat-treating the shaped catalyst pieces at 200°-400° C., preferably 300°-375° C., after the drying but before the treatment with hydrogen fluoride. During this heat treatment, anions which decompose, for example the nitrate anion, are destroyed and the subsequent conversion into the fluoride anion is in this way facilitated.

The amount of hydrogen fluoride employed for the treatment is not critical. Fully active catalysts are already obtained if 2 mol of hydrogen fluoride per mol of metal compound employed are present for the treatment. Higher amounts of hydrogen fluoride are also possible; their use is limited only by economic considerations. The duration of the treatment with hydrogen fluoride can be selected within wide limits; this time is preferably set at 0.5-10 hours. To avoid undesirable temperature peaks, the hydrogen fluoride can be diluted by an inert gas, such as nitrogen or air. The increase in gas volume associated with the inert gas dilution is furthermore suitable for accomodating the water formed and other volatile treatment products. In the case where such a treatment is carried out in a circulating air process, these volatile treatment products are withdrawn more rapidly from the catalyst. Such a treatment with hydrogen fluoride is advantageously carried out in the same apparatus in which the catalyst will finally be employed.

On the basis of their mechanical stability, the catalysts thus obtained are suitable for use in fixed bed, moving bed and fluidized bed reactors.

The catalysts according to the invention can in principle also be used without added promoter; however, the addition of such promoters in many cases has the effect of a further significant increase in activity and selectivity. Inert additives may help to influence the overall kinetics of the fluorination reaction of organic compounds, for example diffusion, adsorption or desorption processes of the reaction partners. This can be effected, for example, by addition of porous inert additives. Inert additives may furthermore be suitable for effecting a dilution effect on the active catalyst constituents in the shaped catalyst pieces and in this way effecting a moderating influence on the fluorination reaction. The essential metal contents are in all cases uniformly randomly distributed in the active substance of the catalyst. For most intended uses, the use of a catalyst according to the invention which is free from inert additives is adequate and therefore preferred.

The invention furthermore relates to the lanthanide catalysts mentioned above under b) consisting of at least one compound of the lanthanides with or without catalyst supports.

To prepare the catalysts under b) according to the invention, oxidic compounds of the lanthanides can be used as starting substances, or lanthanide compounds can be deposited on a suitable catalyst support. Lanthanide elements are understood as the elements of atomic number 57-71; of these, the compounds of cerium, lanthanum, neodymium, ytterbium and dysprosium may be mentioned as preferred. Mixtures of lanthanide compounds can also be employed.

In the case where the catalysts according to the invention are employed in the form of supported catalysts, $Al_2O_3$, $AlF_3$, active charcoal, coke, $MgF_2$, $CaF_2$ and $ZnF_2$ may be mentioned as preferred supports. It is of course also possible for more than one lanthanide compound and more than one support to be present in the catalysts according to the invention.

Such catalysts are prepared by methods which are known in principle. Thus, an economic method comprises grinding lanthanide oxides, mixing them intimately with lubricants and mould release agents, shaping the mixtures by the methods customary in catalyst preparation technology and in general then drying the catalysts.

In the case where the catalysts under b) according to the invention are present on supports, the supports mentioned can be impregnated or sprayed with compounds of the lanthanide elements; this is followed, likewise in the customary manner, by drying.

Active catalysts are likewise obtained if compounds of the lanthanides, for example the carbonates or nitrates, are at least partially converted into oxidic compounds by heating. The activity of the catalysts can be increased by promoters, for example compounds of Cu, Mn or Fe.

It has been observed that the catalysts under b), like those under a), show a significant increase in activity after a short time during their first use. It has now been found that fully active catalysts are already obtained at the start of the first use if the dried shaped catalyst pieces or catalyst powder is treated with excess hydrogen fluoride at a temperature of 20°–500° C., preferably 100°–500° C., particularly preferably 120°–420° C., and then used. The treatment temperature is chosen so that the volatile treatment products do not condense.

The amount of hydrogen fluoride used for the treatment is not critical. Active catalysts are already obtained if 2 mol of hydrogen fluoride per mol of lanthanide compound employed are used for the treatment. Higher amounts of hydrogen fluoride are also possible; their use is limited only by economic considerations. The treatment time is preferably 0.5–10 hours. So that the water formed during the treatment and other volatile reaction products are removed more quickly and undesirable temperature peaks are avoided, the hydrogen fluoride can be diluted by an inert gas, for example by $N_2$ or air. The treatment with hydrogen fluoride for activation of the catalyst can advantageously be carried out in the same apparatus in which the catalyst is later employed.

In another improvement of the treatment of the catalysts with hydrogen fluoride, it has been found that the shaped catalyst pieces are heat-treated at 200°–400° C., preferably 300°–375° C., after the drying but before the hydrogen fluoride treatment. In this procedure, anions, such as the nitrate anion, can be destroyed and their volatile decomposition products removed.

If catalysts under b) according to the invention are prepared as supported catalysts, it may be desirable for the lanthanide compounds impregnated on or sprayed on to be precipitated in the form of the hydroxide by treatment with aqueous alkaline solutions of alkali metal compounds or ammonium compounds, preferably with aqueous ammonia, and in this way to be fixed on the catalyst support.

The content of lanthanide compounds is 0.1–100% by weight of the total weight of the catalyst. The 100% level here is based on the support-free catalyst, whereas values below 100% apply to catalysts containing support and containing promoter. The weight of lanthanide compounds is preferably 2–30% by weight of the total weight of a catalyst according to the invention and containing a support.

The catalysts according to the invention are suitable for use in fixed bed, moving bed and fluidized bed reactors.

The process for exchanging halogen other than fluorine, in particular chlorine, for fluorine is preferably carried out in the gas phase at a temperature of 100°–500° C.

Examples of organic compounds which can be subjected to such a reaction are halogenated, preferably chlorinated, hydrocarbons, halogenated (chlorinated) ketones, halogenated (chlorinated) ethers, halogenated (chlorinated) cyclic acetals, carboxylic acid (ortho-) halides (chlorides), halogenated (chlorinated) nitriles, acid halides (chlorides), chlorinated heterocyclic compounds and others. The process according to the invention is particularly important for halogen (chlorine)-fluorine exchange in halogenated (chlorinated) hydrocarbons, for example in perchlorinated straight-chain or branched alkanes, alkenes or alkadienes having 2–8 C atoms or in perchlorinated cycloalkenes or cycloalkadienes having 4–7 C atoms. The preparation of tetrafluorodichloro-cyclobutene from hexachloro-butadiene and HF in the process according to the invention may be singled out.

In an advantageous variant, the fluorination mixture also contains, in addition to hydrogen fluoride, elemental chlorine or bromine, preferably elemental chlorine, in an amount of 0.1–1.5 mol, preferably 0.2–1.1 mol, per mol of the organic compound to be reacted.

With open-chain or cyclic perhalogenated $C_4$-alkenes or -alkadienes to be reacted it has been observed that the addition of elemental halogen can be used to favour the formation of the open-chain $C_4$-structure. This favouring influence increases as the amount of elemental halogen (chlorine) increases and is only minor in the lower part of the range stated. This is a suitable measure for controlling the product spectrum.

EXAMPLE 1

2.5 parts by weight of $Bi(NO_3)_3.5\ H_2O$ and 1.2 parts of 65% strength nitric acid were dissolved in 3.6 parts of water. 1 part of $Fe(NO_3)_3.9\ H_2O$ was added. This solution was added to 1.5 parts of magnesium oxide and the pasty mass thereby formed was intimately kneaded. The pasty reaction product was then granulated and the granules were dried at 100° C. for 16 hours. The catalyst was then heated at 400° C. for 6 hours. The atomic ratio of Mg:Bi:Fe was 1:0,137:0,066.

0.33 l of the contact body was treated with 5 mol of hydrogen fluoride at 350° C. in a tube of 5 cm internal diameter and 100 cm length. The duration of the hydrogen fluoride treatment was about 3 hours. During this treatment, HF was diluted with $N_2$ in the molar ratio of 1:2.

102 g of hexachlorocyclopentadiene, 210 g of HF and 3 l of chlorine were passed over 200 ml of this catalyst at 350° C. in the course of 5 hours. The reaction gases were condensed in an ice-water mixture. 724 g of an organic phase were deposited and, according to analysis by gas chromatography (GC), contained 58.4% of 1,2-dichloro-3,3,4,4,5,5-hexafluorocyclopentene, 29.1% of 1,2,4-trichloro-3,3,4,5,5-pentafluorocyclopentene and 8.1% of 1,2,4,4-tetrachloro-3,3,5,5-tetrafluorocyclopentene. The hexachlorocyclopentadiene had reacted completely.

EXAMPLE 2

110.4 g of $BiCl_3$ were dissolved in 150 g of 18% strength hydrochloric acid. A solution of 16.76 g of $FeCl_3.6\ H_2O$ in 30 g of water was mixed with this solution. 250 g of MgO were initially introduced into a kneader and the bismuth-iron salt solution was gradually added. The water evaporated due to the exothermic reaction, and was replaced by 170 ml of $H_2O$. After a kneading time of 1.5 hours, the mass was dried and ground, 2% of graphite were added and the mixture was pelletized. The atomic ratio of Mg:Bi:Fe was 1:0.06:0.01. The catalyst was pretreated with HF as in Example 1.

99.6 g of hexachlorobutadiene, 120 g of HF and 22 g of chlorine were passed over 200 ml of this catalyst at 420° C. in the course of 5 hours. The reaction gases were condensed as in Example 1. An organic phase of 81.5 g was formed and, according to GC analysis, contained 73.6% of 2,3-dichloro-1,1,1,4,4,4-hexafluorobut-2-ene, 5.7% of 2-chloro-1,1,1,3,4,4,4-heptafluorobutene and only 6.1% of hexachlorobutadiene.

EXAMPLE 3

In accordance with the procedure of Example 2, a catalyst was prepared from 30 g of 18% strength hydrochloric acid, 20 g of BiCl$_3$, 150 g of water, 94.6 g of FeCl$_3$.6 H$_2$O and 250 g of MgO and was activated.

The atomic ratio of Mg:Bi:Fe was 1:0.01:0.06.

99.6 g of hexachlorobutadiene, 110 g of HF and 27 g of chlorine were passed over 200 ml of catalyst at 425° C. After condensation of the reaction gases, GC analysis of the organic phase weighing 82.1 g gave the following values: 5.9% of 2-chloro-1,1,1,3,4,4,4-heptafluorobutene, 11.3% of 2-chloro-1,1,1,4,4,4-hexafluorobutene, 72.9% of 2,3-dichloro-1,1,1,4,4,4-hexafluorobutene and 4.9% of hexachlorobutadiene.

EXAMPLE 4

In accordance with the procedure of Example 2, a catalyst was prepared from 30 g of 18% strength hydrochloric acid, 20 g of BiCl$_3$, 320 g of water, 16.76 g of FeCl$_3$.6 H$_2$O and 250 g of MgO and was activated.

The atomic ratio of Mg:Bi:Fe in the catalyst was 1:0.01:0.01.

99.6 g of hexachlorobutadiene, 127.2 g of HF and 27 g of chlorine were passed over 220 ml of catalyst at 420° C. in the course of 5 hours. On absorption of the reaction gases in ice-water, 77.03 g of an organic phase were formed, which contained 69.3% of 2,3-dichloro-1,1,1,4,4,4-hexafluorobut-2-ene, 5.6% of 2-chloro-1,1,1,3,4,4,4-heptachlorobut-2-ene and 9.2% of hexachlorobutadiene.

EXAMPLE 5

In accordance with the procedure of Example 1, a catalyst which was produced from a total of 216 g of water, 3 g of nitric acid, 40.9 g of Bi(NO$_3$)$_3$.5 H$_2$O, 278.7 g of Fe(NO$_3$)$_2$.9 H$_2$O and 500 g of MgO was prepared and activated.

The atomic ratio of Mg:Bi:Fe in the catalyst was 1:0.007:0.05.

100.2 g of hexachlorobutadiene and 120 g of HF were passed over 200 ml of catalyst at 410° C. for 5 hours. On condensing the reaction gases in ice-water, 64.3 g of an organic phase were formed which contained 16.3% of 2-chloro-1,1,1,4,4,4-hexafluorobut-2-ene, 9.2% of 2,3-dichloro-hexafluorobut-2-ene, 30.2% of 1,2-dichloro-3,3,4,4-tetrafluorocyclobut-1-ene, 12.6% of 1,2,3-trichloro-3,4,4-trifluorocyclobut-1-ene, 8.6% of tetrachlorodifluoro-cyclobut-1-ene and 8.2% of hexachlorobutadiene.

EXAMPLE 6

In accordance with the procedure of Example 1, a catalyst was prepared from 295 g of water, 25 g of 65% strength nitric acid, 50 g of Fe(NO$_3$)$_3$.9 H$_2$O, 340 g of Bi(NO$_3$)$_3$.5 H$_2$O and 500 g of barium oxide and was activated with HF at 370° C.

The atomic ratio of Ba:Bi:Fe was 1:0.007:0.05.

102 g of hexachlorocyclopentadiene, 125 g of HF and 27 g of chlorine were passed over 200 ml of catalyst at 400° C. in the course of 5 hours. 95.5 g of organic phase were formed which contained 5.1% of 1,2,4-trichloro-3,3,4,5,5-pentafluorocyclopent-1-ene, 64.8% of 1,2,4,4-tetrachloro-3,3,5,5-tetrafluoro-cyclopent-1-ene, 7.4%of1,2,4,4-pentachloro-3,3,5,5-trifluoro-cyclopent-1-ene, 10.1% of 1,2,4,4-hexachloro-3,3,5,5-difluorocyclopent-1-ene and 1.6% of hexachlorocyclopentadiene.

EXAMPLE 7

In accordance with the procedure of Example 1, a catalyst was prepared from 295 g of water, 25 g of 65% strength HNO$_3$, 340 g of Bi(NO$_3$)$_3$.5 H$_2$O, 50 g of Fe(-NO$_3$)$_3$.9 H$_2$O and 500 g of calcium oxide and was activated with HF at 270° C.

Approximate molar ratio of Ca:Bi:Fe= 1:0.08:0.02.

149.4 g of hexachlorobutadiene, 111 g of HF and 49 g of chlorine were passed over 130 ml of this catalyst at 440° C. in the course of 3 hours. On condensing the reaction gases in ice-water, 138 g of an organic phase were formed, which contained 51.3% of hexachlorobutadiene, 5.6% of trichloro-trifluoro-cyclobutene, 11.3% of dichlorotetrachlorocyclobutene and 18.7% of a component C$_6$Cl$_5$F.

EXAMPLE 8

A catalyst was prepared and activated according to Example 1 from 25 g of 65% strength HNO$_3$, 500 g of water, 340 g of Bi(NO$_3$)$_3$.5 H$_2$O, 100 g of Mn(NO$_3$)$_2$.6 H$_2$O and 270 g of MgO.

Molar ratio of Mg:Bi:Mn=1:0.10:0.05.

79.7 g Of hexachlorobutadiene, 140 g of HF and 7.2 g of chlorine were passed over 130 ml of this catalyst at 410° C. in the course of 4 hours. On condensing the reaction gases in ice-water, 59.8 g of an organic phase were formed which, according to GC analysis, contained 5.8% of 2,3-dichloro-1,1,1,4,4,4-hexafluorobut-2-ene, 11.9%of 1,2-dichloro-3,3,4,4-tetrafluorocyclobut-1-ene, 23.1% of 1,2,3-trichloro-3,4,4-trifluorocyclobut-1-ene and 14.7% of tetrachloro-difluorocyclobutene, as well as 13.9% of hexachlorocyclobutadiene.

EXAMPLE 9

In accordance with Example 1, a catalyst was prepared from 370 g of MgO, 251.6 g of Bi(NO$_3$)$_3$.5 H$_2$O, 18.5 g of 65% strength nitric acid and 100 g of water and was activated with HF.

Molar ratio: Mg:Bi=1:0.056;

99.6 g of hexachlorobutadiene, 175 g of HF and g of chlorine were passed over 130 ml of the catalyst at 365° C. in the course of 5 hours. 71.4 g of an organic phase were formed, which contained 3.7% of 2,3-dichloro-1,1,1,4,4,4-hexafluorobut-2-ene, 12.7% of 1,2-dichloro-3,3,4,4-tetrafluorocyclobut-1-ene, 27.4% of 1,2,3-trichloro-3,4,4-trifluorocyclobut-1-ene, 14.5% of tetrachloro-difluoro-cyclobutene and 24.8% of hexachlorobutadiene.

EXAMPLE 10

A catalyst was prepared from the following components in accordance with the procedure of Example 1: 418 g of water, 25 g of 65% strength HNO$_3$, 340 g of Bi(NO$_3$)$_3$.5 H$_2$O, 50 g of Co(NO$_3$)$_2$.6 H$_2$O and 500 g of MgO.

Atomic ratio of Mg:Bi:Co=1:0.05:0.01.

9.6 g of a vaporized mixture of 61% of tetrachloropyrimidine and 39% of toluene and 30 g of HF were passed per hour over 200 ml of catalyst at 470° C. The reaction product contained, calculated on a toluene-free basis, 67.9% of 5-chloro-2,4,6-trifluoropyrimidine and 22.8% of dichloro-difluoropyrimidine. The tetrachloropyrimidine had reacted completely.

EXAMPLE 11

In accordance with the catalyst preparation according to Example 1, a catalyst was produced from 360 g of water, 120 g of 65% strength nitric acid, 250 g of Bi(-NO$_3$)$_3$.5 H$_2$O, 107.3 g of Ce(NO$_3$)$_3$.6 H$_2$O and 500 g of MgO and was activated.

The atomic ratio of Mg:Bi:Ce was 1:0.04:0.02.

49.7 g of benzotrichloride and 79.5 g of HF were passed over 130 ml of this catalyst at 360° C. in the course of 3 hours. On condensing the reaction gases, 36.2 g of an organic phase were obtained, which contained 91.7% of benzotrifluoride, 2.9% of chlorodifluoromethyl-benzene and 1.6% of benzotrichloride.

EXAMPLE 12

78.5 g (0.363 mol) of tetrachloropyrimidine and 94 g of HF were passed over 220 ml of a catalyst, which had been prepared in accordance with Example 2, at 435° C. in the course of 10 hours. On condensing the reaction gases, 54 g of an organic phase was formed, which contained 0.13 mol of 5-chloro-2,4,6-trifluoropyrimidine, 0.102 mol of dichloro-difluoro-pyrimidine, 0.057 mol of trichloromonofluoropyrimidine and 0.0245 mol of tetrachloropyrimidine.

EXAMPLE 13

20 g of $BiCl_3$ were dissolved in 30 g of 18% strength hydrochloric acid and 16.76 g of $FeCl_3.6\ H_2O$ were dissolved in 150 g of water. The two solutions were combined and were gradually kneaded intensively with 250 g of magnesium oxide, a further 170 ml of water being added. The material was dried at 100° C. in vacuo and comminuted and the fraction of particle size 2–5 mm was sieved out. This catalyst was activated by treatment with HF at 350° C. for 5 hours.

102 g of hexachlorocyclopentadiene and 201.5 g of HF were passed over 220 ml of the catalyst at 415° C. in the course of 5 hours. On condensing the reaction gases in cold water, 68.9 g of an organic phase were formed, which contained 8.5% of 1,2-dichloro-3,3,4,4,5,5-hexafluorocyclopent-1-ene, 16.3% of 1,2,4-trichloro-3,3,4,5,5-pentafluorocyclopent-1-ene, 23.8% of tetrachloro-tetrafluoro-cyclopentene, 18.4% of pentachloro-trifluoro-cyclopentene, 13.3% of mono- and difluoro-polychloro-cyclopentene and 9.7% of hexachlorocyclopentadiene.

EXAMPLE 14

81.6 g of hexachlorocyclopentadiene, 108 g of HF and 10.8 g of chlorine were passed over 220 ml of the catalyst of Example 4 at 415° C. in the course of 4 hours. On absorption of the reaction gases in water, 73.6 g of an organic phase were formed, which contained 3.8% of 1,2-dichloro-3,3,4,4,5,5-hexafluorocyclopent-1-ene, 15.6% of 1,2,4-trichloro-3,3,4,5,5-pentafluorocyclopent-1-ene, 33.7% of 1,2,4,4-tetrachloro-3,3,5,5-tetrafluorocyclopent-1-ene, 17.0% of pentafluoro-trifluorocyclopent-1-ene, 13% of di- and monofluoro-chlorocyclopent-1-ene and 6.6% of hexachlorocyclopentadiene.

EXAMPLE 15

650 g of cerium(IV) oxide were kneaded with 650 g of a 2% strength polyvinyl alcohol solution for 1 hour. The lumps formed during this procedure were dried at 100° C. in vacuo, comminuted and sieved.

200 ml of this catalyst of particle size between 2 and 5 mm were treated with 22 g/hour of HF at 360° C. for 7 hours. 100 g of hexachlorobutadiene, 150 g of HF and 9 g of chlorine were then passed at 410° C. in the course of 5 hours. The reaction gases were condensed in an ice-water mixture. 68.4 g of an organic phase were formed, which contained 44.5% of 2,3-dichloro-1,1,1,4,4,4-hexafluorobut-2-ene, 25.3% of 1,2-dichloro-3,3,4,4-tetrafluoro-cyclobut-1-ene, 8.1% of 1,2,3-trichloro-3,4,4-trifluorocyclobut-1-ene and 6.5% of hexachlorobutadiene.

EXAMPLE 16

162.4 g of $La(NO_3)_3.6\ H_2O$ were dissolved in 255 g of water. 500 ml of aluminium oxide were impregnated with this solution. The catalyst was dried at 70° C. in vacuo and heated at 380° C. for 18 hours. 20 g/hour of HF were then passed over 110 ml of this catalyst at 360° C. for 8 hours. 150 g of hexachlorobutadiene, 120 g of HF and 39 g of chlorine were passed over at 365° C. in the course of 3 hours. On absorption of the reaction gases in ice-water, 102.3 g of organic phase were formed, which contained 42.8% of hexachlorobutadiene, 31.5% of 2,3-dichloro-1,1,1,4,4,4-hexafluorobut-2-ene, 3.1% of 1,2-dichloro-3,3,4,4-tetrafluorocyclobut-1-ene, 4% of 1,2,3-trichloro-3,4,4-trifluorocyclobut-1-ene and 6.2% of tetrachlorodifluorobutenes.

EXAMPLE 17

In accordance with Example 2, a catalyst was prepared from 162.8 g of $Ce(NO_3)_3.6\ H_2O$, 255 g of water and 500 ml of aluminium oxide SAS 350 and was activated.

100 g of hexachlorocyclopentadiene, 200 g of HF and 9 g of chlorine were passed over 120 ml of this catalyst at 410° C. in the course of 5 hours. On absorption of the reaction gases in ice-water, 87.5 g of an organic phase were formed, which contained 2.1% of 1,2-dichloro-3,3,4,4,5,5-hexafluorocyclopent-1-ene, 23.8% of 1,2,4-trichloro-3,3,4,5,5-pentafluorocyclopent-1-ene, 35.1% of 1,2,4,4-tetrachloro-3,3,5,5-tetrafluorocyclopent-1-ene and 3% of hexachlorocyclopentene.

EXAMPLE 18

In accordance with the procedure of Example 2, a catalyst was prepared from 100 g of $Dy(NO_3)_3.5\ H_2O$, dissolved in 300 g of water, and 500 ml of granular 4 mm A charcoal. The granules were dried at 100° C. in vacuo. The dried granules were introduced into 3 l of a 5% strength aqueous ammonia solution and the mixture was heated at 70° C. for 1 hour. The granules were filtered off, washed in several portions with 5 l of water and finally dried at 150° C.

120 g of HF were passed over 120 ml of this catalyst at 360° C. for 5 hours.

219.6 g of benzoyl chloride and 265 g of HF were passed over at 410° C. for 5 hours. The reaction gases were condensed in an ice-water mixture. 183.5 g of an organic phase were formed, which contained 95.6% of benzoyl fluoride, 3.4% of benzoic acid and 0.1% of benzoyl chloride.

EXAMPLE 19

500 g of $Ce(NO_3)_3.6\ H_2O$ were melted at 70°–90° C. 35 g of $Fe(NO_3)_3.9\ H_2O$ were dissolved in the melt. This homogeneous mixture was heated. Water escaped in the temperature range around 150° C., and at higher temperatures nitrous gases and solids were formed. Finally, the mass was heat-treated at 500° C. for 5 hours.

After cooling, the mass was ground, 2% of graphite was added to the powder and the mixture was pressed to 4 mm pellets.

The catalyst was treated with HF at 350° C. for 6 hours in order to effect activation.

127.4 g of perchloropropene and 159.0 g of HF were passed over 80 ml of the catalyst at 400° C. in the course of 5.5 hours. The reaction gases were condensed in an ice-water mixture. 98.8 g of an organic phase were formed, which contained 1.85% of 1,1,1,3,3,3-hexafluoro-2-chloro-propane, 11.3% of tetrachloro-propene, 85.2% of trichloro-trifluoropropene and 0.1% of perchloropropene.

EXAMPLE 20

In accordance with the instructions of Example 19, a catalyst was prepared from 500 g of $Ce(NO_3)_3.6\ H_2O$ and 19.3 g of $Cu(NO_3)_2.\ H_2O$ and was activated.

169.9 g of perchloropropene and 122.2 g of HF were passed over 120 ml of this catalyst at 395° C. in the course of 3.16 hours. On condensing the reaction gases in an ice-water mixture, 111.2 g of an organic phase were formed, which contained 0.5% of perchloropropene, 1.5% of 1,1,1,3,3,3-hexafluoro-2-chloropropane, 12.1% of 1,1,1,3-tetrafluoro-2,3-dichloropropene and 83.7% of trifluoro-trichloropropene.

I claim:

1. A process for exchanging halogen other than fluorine, for fluorine in an organic compound by means of hydrogen fluoride in the presence of a chromium-free bismuth/alkaline earth metal catalyst which contains 0.005-0.8 g-atom of bismuth per mol of the alkaline earth metal compound employed.

2. The process of claim 1, wherein chlorine is exchanged for fluorine.

3. The process of claim 1, wherein the bismuth/alkaline earth metal catalysts contain 0.008-0.7 g-atom of bismuth per mol of the alkaline earth metal compound employed.

4. The process of claim 1, wherein the organic compound is perchlorinated straight-chain or branched alkane, alkene or alkadiene having 2-8 C atoms or a perchlorinated cycloalkene or cycloalkadiene having 4-7 C atoms.

5. The process of claim 1, wherein the halogen exchange is carried out in the presence of 0.1-1.5 mol of the halogen other than fluorine per mol of the organic compound to be reacted, in elemental form.

6. The process of claim 5, wherein the halogen exchange is carried out in the presence of 0.2-1.1 mol of the halogen other the fluorine per mol of the organic compound.

7. The process of claim 5, wherein the halogen to be exchanged is also used in elemental form in the halogen-fluorine exchange in open-chain or cyclic perhalogenated alkanes and alkadienes having 4 C atoms, in order to favour the open-chain structure of the $C_4$-alkene or $C_4$-alkadiene in which the halogen has been exchanged for fluoride.

* * * * *